US009610240B2

(12) United States Patent
Somboon et al.

(10) Patent No.: US 9,610,240 B2
(45) Date of Patent: Apr. 4, 2017

(54) SHAMPOO COMPOSITION

(71) Applicant: Conopco, Inc., Englewood Cliffs, NJ (US)

(72) Inventors: Attaporn Somboon, Bangkok (TH); Jianfeng Zhang, Shanghai (CN); Christopher John Roberts, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/418,488

(22) PCT Filed: Feb. 25, 2013

(86) PCT No.: PCT/EP2013/053684
§ 371 (c)(1),
(2) Date: Jan. 30, 2015

(87) PCT Pub. No.: WO2014/023440
PCT Pub. Date: Feb. 13, 2014

(65) Prior Publication Data
US 2015/0190334 A1 Jul. 9, 2015

(30) Foreign Application Priority Data

Aug. 6, 2012 (WO) ............... PCT/CN2012/079741
Sep. 21, 2012 (EP) ................................. 12185357

(51) Int. Cl.
*A61Q 5/02* (2006.01)
*A61K 8/898* (2006.01)
*A61Q 5/12* (2006.01)
*A61K 8/891* (2006.01)
*A61K 8/892* (2006.01)
*A61K 8/90* (2006.01)

(52) U.S. Cl.
CPC ............. *A61K 8/898* (2013.01); *A61K 8/891* (2013.01); *A61K 8/892* (2013.01); *A61K 8/90* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| 6,277,361 | B1 * | 8/2001 | Murray | A61K 8/898 424/70.1 |
| 6,610,280 | B2 | 8/2003 | Ainger et al. | |
| 7,183,243 | B2 * | 2/2007 | Ainger | A61K 8/737 424/70.1 |
| 7,459,417 | B2 | 12/2008 | Derici | |
| 7,611,698 | B2 | 11/2009 | Derici | |
| 2001/0031250 | A1 * | 10/2001 | Blount | A61K 8/64 424/70.1 |
| 2003/0224954 | A1 * | 12/2003 | Wells | A61Q 5/12 510/119 |
| 2005/0129643 | A1 | 6/2005 | Lepilleur et al. | |
| 2011/0008266 | A1 * | 1/2011 | Tamarkin | A61K 8/046 424/43 |
| 2013/0125914 | A1 | 5/2013 | Battermann et al. | |

FOREIGN PATENT DOCUMENTS

| CH | WO 2011057882 A1 * | 5/2011 | ............ A61K 8/046 |
| DE | 102010031318 | 1/2012 | |
| EP | 1504748 A1 * | 2/2005 | |
| WO | WO9917713 | 4/1999 | |
| WO | WO03094873 | 11/2003 | |
| WO | WO 2011057882 A1 * | 5/2011 | |

OTHER PUBLICATIONS

IPRP2 in PCTEP21013053684 dated Nov. 13, 2014. In J4246USw-NPLRef1, pp. 1-8.
Mintel, Conditioner, XP55055392, Aug. 1, 2012. In J4246USw-NPLRef1, p. 9-9.
Search Report in PCT/EP2013/053684 dated Apr. 3, 2013. In J4246USw-NPLRef1, pp. 10-13.
Search Report in EP12185357, dated Mar. 6, 2013. In J4246USw-NPLRef1, pp. 14-15.
Written Opinion in PCT/EP2013/053684 dated Aug. 18, 2014. In J4246Sw-NPLRef1, pp. 20-28.

* cited by examiner

*Primary Examiner* — Robert A Wax
*Assistant Examiner* — Quanglong Truong
(74) *Attorney, Agent, or Firm* — Greenberg Traurig, LLP

(57) ABSTRACT

Disclosed is a shampoo composition comprising a silicone component which comprises a dimethiconol, a blend of dimethicone with surface active block copolymer, and further comprises an aminosilicone. The shampoo can provide improved conditioning benefit.

12 Claims, No Drawings

SHAMPOO COMPOSITION

FIELD OF THE INVENTION

The present invention relates to an improved shampoo composition. More particularly, the present invention relates to a shampoo composition comprising a silicone component which comprises a dimethiconol, a blend of dimethicone with surface active block copolymer, and further comprises an aminosilicone. Moreover, the present invention is also related to use of the silicone component for improved conditioning benefit.

BACKGROUND OF THE INVENTION

Silicone has been widely used in hair/scalp compositions as a conditioning agent. Such silicone conditioning agents may bring the benefit of making the hair easier to comb when wet and more manageable when dry, e. g. less static and fly-away.

However, there are still needs to improve the conditioning performance of hair care compositions. Therefore, we have recognized a need for improved shampoo compositions. It has been surprisingly found that by incorporating a silicone component which comprises a dimethiconol, a blend of dimethicone with surface active block copolymer, and further comprises an aminosilicone into a shampoo composition, the conditioning performance will be enhanced.

SUMMARY OF THE INVENTION

In the first aspect, the present invention is directed to a shampoo composition comprising a silicone component which comprises a dimethiconol, a blend of dimethicone with surface active block copolymer, and further comprises an aminosilicone.

In the second aspect, the present invention is directed to a method of treating the hair of an individual comprising the step of topically applying the composition of the present invention to at least a portion of the hair.

In the third aspect, the present invention is directed to use of the silicone component of the present invention for hair conditioning.

All other aspects of the present invention will more readily become apparent upon considering the detailed description and examples which follow.

DETAILED DESCRIPTION

Except in the examples, or where otherwise explicitly indicated, all numbers in this description indicating amounts of material or conditions of reaction, physical properties of materials and/or use may optionally be understood as modified by the word "about".

All amounts are by weight of the final composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

"Size" as used herein refers to the longest length measurable in any dimension in the event the particle is not a perfect sphere. Particle size can be measured, for example by dynamic light scattering (DLS).

"Non-volatile" as used herein means having vapour pressure from 0 to 0.1 mm Hg (13.3 Pa), preferably from 0 to 0.05 mm Hg, more preferably from 0 to 0.01 mm Hg at 25° C.

Viscosity for the purposes of the present invention means kinematic viscosity at 25° C. and is reported as centiStokes (1 cSt=1 mm$^2$·s$^{-1}$). Viscosity of fluids such as silicone can be determined, for example, by the relevant international standard, such as ISO 3104.

Silicone Component

For the avoidance of doubt, all amounts of silicone component refer to the amount of all silicones in the component, not including other ingredient, for example the surface active block copolymer.

Typically, the silicone component is present in the composition in amount from 0.01 to 10% by weight of the composition, more preferably from 0.1 to 5% by weight of the composition, even more preferably from 0.3 to 4%, still even more preferably from 0.5 to 3% and most preferably from 0.7 to 2.5% by weight of the composition.

The weight ratio of dimethiconol to dimethicone is preferably in the range from 1:100 to 5:1, more preferably from 1:10 to 7:5, ever more preferably from 1:5 to 4:3, most preferably from 1:2 to 6:5.

The weight ratio of dimethiconol to aminosilicone is preferably in the range of 1:100 to 20:1, more preferably from 1:20 to 5:1. Even more preferably, the weight ratio of dimethiconol to aminosilicone is in the range of 1:10 to 3:1, most preferably from 1:5 to 1:2.

The weight ratio of dimethicone to aminosilicone is preferably in the range of 1:100 to 20:1, more preferably from 1:10 to 10:1. Even more preferably, the weight ratio of dimethicone to aminosilicone is in the range of 1:5 to 2:1, most preferably from 1:2 to 3:2.

Preferably, the $D_{3,2}$ average particle diameter ratio of dimethiconol to dimethicone is from 1:500 to 1:5, more preferably from 1:100 to 1:15, most preferably from 1:80 to 1:30.

Preferably, the $D_{3,2}$ average particle diameter ratio of dimethiconol to aminosilicone is from 1:10 to 5:1, more preferably from 1:4 to 1:1, most preferably from 1:3 to 4:5. Preferably, the $D_{3,2}$ average particle diameter ratio of dimethicone to aminosilicone is from 5:1 to 100:1, more preferably from 10:1 to 50:1, most preferably from 20:1 to 30:1.

Preferably, the silicone component comprises from 10 to 80% of dimethiconol by weight of the component, more preferably from 20 to 60%, even more preferably from 35 to 54%, still even more preferably from 30 to 50% by weight of the component.

Preferably, the silicone component comprises from 10 to 80% of dimethicone by weight of the component, more preferably from 20 to 60%, even more preferably from 30 to 50% by weight of the component.

Preferably, the silicone component comprises from 1 to 60% of aminosilicone by weight of the component, more preferably from 8 to 55%, even more preferably from 15 to 40%, still even more preferably from 22 to 35% by weight of the component.

The silicone component is preferably present in the composition in of amount at least 10% by weight of the total silicone in the composition, more preferably from 30 to 100% by weight of the total silicone in the composition. Most preferably, the total silicone in the shampoo consists essentially of, or consists of the dimethiconol, the blend of dimethicone with surface active block copolymer and the aminosilicone.

Preferably, the silicone component is silicone conditioning agent.

Dimethiconol

Preferably the dimethiconol is emulsified with nonionic and/or anionic surfactant. Preferably, the dimethiconol is non-volatile.

Preferably, the dimethiconol is present in the composition in amount from 0.001 to 4% by weight of the composition, more preferably from 0.01 to 3%, even more preferably from 0.04 to 2%, still even more preferably from 0.15 to 1.2%, most preferably from 0.2 to 0.8% by weight of the total composition.

The viscosity of the dimethiconol itself (not the emulsion or the final shampoo composition) is typically from 10,000 to $10^9$ cSt (centi-Stokes) at 25° C., preferably from 60,000 cSt to 500,000,000 cSt, more preferably from 100,000 to 50,000,000 cSt, even more preferably from 200,000 to 5,000,000 cSt, and most preferably from 500,000 to 2,000,000 cSt.

Example of suitable emulsified dimethiconol for use in the compositions of the invention has a $D_{3,2}$ average particle diameter in the composition of less than 20 micron, preferably from 5 nm to 5 micron, more preferably from 20 nm to 2 micron, even more preferably from 40 nm to 1 micron, most preferably from 100 to 500 nm.

Silicone $D_{3,2}$ mean droplet diameter may be measured by means of a laser light scattering technique, for example using a 2600D Particle Sizer from Malvern Instruments.

Examples of suitable pre-formed emulsions include DC 5-7051, DC 1788, DC 1785 available from Dow Corning. The most preferred dimethiconol is DC 1788.

Blend of Dimethicone with Surface Active Block Copolymer

The blend of dimethicone with surface active block copolymer typically exists as discrete, dispersed droplets comprising a dimethicone with mean diameter of the droplets (D3,2) from 0.2 to 100 micrometers and a surface active block copolymer with a mean molecular weight of 4000 unified atomic mass units or more comprising polyethyleneoxide blocks and polypropyleneoxide blocks, wherein each block consists of 2 or more ethylene oxide or propylene oxide monomer units and wherein the mean number propylene oxide monomer units in the block copolymer is 25 or more.

One preferred form of the surface active block copolymer has formula I and has the CTFA designation Poloxamer. These are commercially available under the trade name "Pluronic" from BASF.

   I

Suitably, the mean value of x in formula I is 4 or more, preferably 8 or more, more preferably 25 or more, yet more preferably 50 or more and most preferably 80 or more. Suitably, the mean value of y is 25 or more, preferably 35 or more, more preferably 45 or more and most preferably 60 or more.

Another preferred form of the surface active block copolymer is according to formula II and has the CFTA designation Poloxamine. Those are commercially available under the trade name "Tetronic" from BASF.

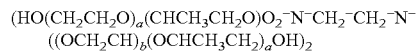   II

Suitably, the mean value of a is 2 or more, preferably 4 or more, more preferably 8 or more, even more preferably 25 or more and most preferably 40 or more. The mean value of b is suitably 6 or more, preferably 9 or more, more preferably 11 or more and most preferably 15 or more.

In formula I, the degree of polymerisation, x, is indicated as the same for each polyethyleneoxide block. This is also the case in formula II for a and b for the EO and PO blocks respectively. For the sake of clarity, it should be explained that these degrees of polymerisation are mean values and are approximately the same rather than identical for any particular formula. This is a result of the polymerisation methods used for production of the compounds and known to those skilled in the art of polymer synthesis.

Preferably, the molecular weight of the block copolymer is suitably 4000 unified atomic mass units or more, preferably 7000 or more, more preferably 10000 or more, most preferably 12000 or more.

The mean molecular weight is suitably measured by determining the hydroxyl number for the polymer then transforming this into molecular weight. This corresponds to a number based mean molecular weight.

Preferably, the surface active block copolymer is poloxamer and/or poloxamine, more preferably, the surface active block copolymer is poloxamer.

The weight ratio of dimethicone to surface active block copolymer in the blend is preferably in the range from 2:1 to 200:1, more preferably from 5:1 to 50:1, even more preferably from 10:1 to 40:1, most preferably from 15:1 to 30:1.

The dimethicone suitable for use in the compositions of the invention preferably has a $D_{3,2}$ average particle diameter in the composition of from 0.2 to 100 micron, preferably from 0.5 to 30 micron, more preferably from 2 to 20 micron, even more preferably from 5 to 15 micron, and most preferably from 7 to 12 micron.

Silicone D3,2 mean droplet diameter may be measured by means of a laser light scattering technique, for example using a 2600D Particle Sizer from Malvern Instruments.

Preferably, the dimethicone itself (not the blend) is present in the composition in amount from 0.001 to 4% by weight of the composition, more preferably from 0.04 to 3%, even more preferably from 0.1 to 2%, still even more preferably from 0.15 to 0.7%, most preferably from 0.2 to 0.5% by weight of the total composition.

Preferably, the dimethicone is present in the blend in amount from 10 to 89% by weight of the blend, more preferably from 25 to 80%, even more preferably from 35 to 75%, and most preferably from 48% to 68% by weight of the blend.

Preferably, the surface active block copolymer is present in the blend in amount from 0.1 to 15% by weight of the blend, more preferably from 0.5 to 8%, even more preferably from 1 to 5%, and most preferably from 2.5% to 3.5% by weight of the blend.

Preferably, the blend may further comprise non-ionic and/or anionic surfactant from 0.1 to 20% by weight of the blend, more preferably from 2 to 10% by weight of the blend.

Preferably, the dimethicone is emulsified with the surfactant in the blend.

Preferably, the blend also comprises water at from 10 to 89% by weight of the blend, more preferably from 30 to 70% wt. and most preferably from 40 to 60% by weight of the blend.

The dimethicone is water-insoluble. By water-insoluble is meant that the solubility in water at 25° C. is 0.01% by weight or less. Preferably the dimethicone is non-volatile.

The viscosity of the dimethicone itself (not the emulsion or the final shampoo composition) is preferably from 1,000 to 10,000,000 cSt (centi-Stokes) at 25° C., more preferably from 5,000 to 1,000,000 cSt, even more preferably from 15,000 to 300,000 cSt, and most preferably from 30,000 to 100,000 cSt. Suitable methods for measuring the kinematic viscosity of silicone oils are known to those skilled in the art, e.g. capillary viscometers. For high viscosity silicones, a constant stress rheometer can be used to measure viscosity.

The blend of silicone with surface active block copolymer is preferably made by:
i) preparing an oil-in-water emulsion of a silicone conditioning oil, and
ii) dispersing the surface active block copolymer into the emulsion.

Suitable emulsifiers for use in the preparation of the aqueous emulsion are well known in the art and include anionic, cationic, zwitterionic, amphoteric and nonionic surfactants, and mixtures thereof. Examples of anionic surfactants used as emulsifiers for the silicone particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20, alkylphenol ether sulphates, e.g., octylphenol ether sulphate nEO where n is from 1 to 20, and sulphosuccinates, e.g., sodium dioctylsulphosuccinate.

Examples of nonionic surfactants suitable for use as emulsifiers for the silicone droplets are alkylphenol ethoxylates, e.g., nonylphenol ethoxylate nEO, where n is from 1 to 50 and alcohol ethoxylates, e.g., lauryl alcohol nEO, where n is from 1 to 50, ester ethoxylates, e.g., polyoxyethylene monostearate where the number of oxyethylene units is from 1 to 30.

Aminosilicone

Aminosilicone means a silicone comprising at least one primary, secondary or tertiary amine group, or a quaternary ammonium group. Suitable aminosilicone is described in EP 455,185 (Helene Curtis) and include trimethylsilylamodimethicone as depicted below, and are sufficiently water insoluble so as to be useful in compositions of the invention:

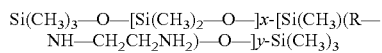

wherein x+y is a number from about 50 to about 500, and the mole % amine functionality is in the range of from 0.3 to 8%, preferably from 0.5 to 4%, and wherein R is an alkylene group having from 2 to 5 carbon atoms. Preferably, the number x+y is in the range of from about 100 to about 300, and the mole % amine functionality is in the range of from about 1.5 to about 6%.

Preferably, the aminosilicone is amino functional polysiloxanes having the CTFA designation "amodimethicone".

Preferably, the aminosilicone is different from dimethiconol and dimethicone. Preferably, the aminosilicone is non-volatile.

Preferably, the aminosilicone is present in the composition in amount from 0.005 to 4% by weight of the composition, more preferably from 0.01 to 2%, even more preferably from 0.04 to 1%, still even more preferably from 0.1 to 0.7%, most preferably from 0.2 to 0.5% by weight of the total composition.

Preferably, the aminosilicone is emulsified with non ionic and/or cationic surfactant.

The emulsified aminosilicone suitable for use in the compositions of the invention preferably has a $D_{3,2}$ average particle diameter in the composition of from 10 nm to 20 micron, preferably from 30 nm to 5 micron, more preferably from 80 to 2 micron, even more preferably from 120 nm to 1.5 micron, and most preferably from 200 to 800 nm.

The viscosity of the aminosilicone itself (not the emulsion or the final shampoo composition) is typically from 10 to 500,000 cSt (centi-Stokes) at 25° C., preferably from 100 cSt to 200,000 cSt, more preferably from 500 to 20,000 cSt, and even more preferably from 1,000 to 6,000 cSt.

Specific examples of emulsified aminosilicones suitable for use in the invention include, for example, DC 929, DC 939, DC 949, SM 8704C, SM 8904 (all ex Dow Corning).

Cleansing Surfactant

In a preferred embodiment the composition comprises a cleansing surfactant.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic surfactants are the alkyl sulfates and alkyl ether sulfates. These materials have the respective formulae $R_2OSO_3M$ and $R_1O(C_2H_4O)_xSO_3M$, wherein $R_2$ is alkyl or alkenyl of from 8 to 18 carbon atoms, x is an integer having a value of from about 1 to about 10, and M is a cation such as ammonium, alkanolamines, such as triethanolamine, monovalent metals, such as sodium and potassium, and polyvalent metal cations, such as magnesium, and calcium. Most preferably $R_2$ has 12 to 14 carbon atoms, in a linear rather than branched chain.

Preferred anionic cleansing surfactants are selected from sodium lauryl sulphate and sodium lauryl ether sulphate(n)EO, (where n is from 1 to 3); more preferably sodium lauryl ether sulphate(n)EO, (where n is from 1 to 3); most preferably sodium lauryl ether sulphate(n)EO where n=1.

Preferably the level of alkyl ether sulphate is from 0.5 wt % to 25 wt % of the total composition, more preferably from 3 wt % to 18 wt %, most preferably from 6 wt % to 15 wt % of the total composition.

The total amount of anionic cleansing surfactant in compositions of the invention generally ranges from 0.5 wt % to 45 wt %, more preferably from 1.5 wt % to 20 wt %.

Compositions of the invention may contain non-ionic surfactant. Most preferably non-ionic surfactants are present in the range 0 to 5 wt %.

Nonionic surfactants that can be included in compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups. Alkyl ethoxylates are particularly preferred. Most preferred are alkyl ethoxylates having the formula R—(OCH$_2$CH$_2$)$_n$OH, where R is an alkyl chain of C12 to C15, and n is 5 to 9.

Other suitable nonionic surfactants include mono- or di-alkyl alkanolamides. Examples include coco mono- or di-ethanolamide and coco mono-isopropanolamide.

Further nonionic surfactants which can be included in compositions of the invention are the alkyl polyglycosides (APCs). Typically, APG is one which comprises an alkyl group connected (optionally via a bridging group) to a block of one or more glycosyl groups. Preferred APGs are defined by the following formula:

$$RO—(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92/06154 and U.S. Pat. No. 5,194,639, and the N-alkoxy polyhydroxy fatty acid amides, such as $C_{10}$-$C_{18}$N-(3-methoxypropyl) glucamide.

Amphoteric or zwitterionic surfactant can be included in an amount ranging from 0.5 wt % to about 8 wt %, preferably from 1 wt % to 4 wt % of the total composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

Cationic Deposition Polymer

Cationic polymers are preferred ingredients in the shampoo composition of for enhancing performance.

Suitable cationic polymers may be homopolymers which are cationically substituted or may be formed from two or more types of monomers. The weight average (Mw) molecular weight of the polymers will generally be between 100,000 and 2 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo- and co-polymers of unsaturated carboxylic acids having from 3 to 5 carbon atoms, (as described in U.S. Pat. No. 4,009,256);
cationic polyacrylamides (as described in WO95/22311).
Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include monomers of the formula:

A—O—[R—N+(R1)(R2)(R3)X—], wherein: A is an anhydroglucose residual group, such as a starch or cellulose anhydroglucose residual. R is an alkylene, oxyalkylene, polyoxyalkylene, or hydroxyalkylene group, or combination thereof. R1, R2 and R3 independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R1, R2 and R3) is preferably about 20 or less, and X is an anionic counter ion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C135, JAGUAR C14, JAGUAR C15, JAGUAR C17 and JAGUAR C16 Jaguar CHT and JAGUAR C162.

Mixtures of any of the above cationic polymers may be used.

Cationic polymer will generally be present in a shampoo composition of the invention at levels of from 0.01 to 5%, preferably from 0.05 to 1%, more preferably from 0.08 to 0.5% by total weight of cationic polymer based on the total weight of the composition.

Optional Ingredients

The composition may comprise other functional actives for hair care product, for example, anti-dandruff agent.

Antidandruff agents are compounds that are active against dandruff and are typically antimicrobial agents and preferably antifungal agents.

Antifungal agents typically display a minimum inhibitory concentration of about 50 mg/ml or less against *Malassezia* spp.

Suitable antidandruff agents include compounds selected from azole based antifungal agents, octopirox, metal pyrithione salts, and mixtures thereof. The preferred azole based antifungal agents are ketoconazole and climbazole. Preferred metal pyrithione salts are zinc, copper, silver and zirconium pyrithione. The most preferred is zinc pyrithione.

Preferably, the antidandruff agent is present at from 0.01 to 5% wt. of the composition, more preferably from 0.1 to 2.5% wt. of the composition.

The composition of the invention may contain other ingredients for enhancing performance and/or consumer acceptability. Such ingredients include fragrance, dyes and pigments, pH adjusting agents, pearlescers or opacifiers, viscosity modifiers, and preservatives or antimicrobials. Each of these ingredients will be present in an amount effective to accomplish its purpose. Generally these optional ingredients are included individually at a level of up to 5% by weight of the total composition.

Preferably, the composition comprises at least 5% of water by weight of the composition, more preferably from 15 to 95%, even more preferably from 35 to 88%, still even more preferably from 45 to 82%, most preferably from 65 to 80% by weight of the total composition.

Compositions of the invention are primarily intended for topical application to at least a portion of the hair of an individual, either in rinse-off or leave-on compositions, for the treatment of dry and/or wet, damaged and/or unmanageable hair.

The invention will now be described with reference to the following non-limiting examples.

Example 1

Shampoo compositions were made by standard processes and has the formulation given in Table 1.

TABLE 1

| Ingredient % wt | 1 | 2 | 3 | 4 | A | B |
|---|---|---|---|---|---|---|
| Sodium Laureth Sulfate | 13.31 | 13.31 | 13.31 | 13.31 | 13.31 | 13.31 |
| Dimethiconol[1] | 1.64 | 1.09 | 0.55 | 1.50 | 1.80 | — |
| Blend of dimethicone with poloxamer[2] | 1.09 | 1.64 | 2.18 | 1.00 | 1.20 | — |
| Amodimethicone[3] | 0.27 | 0.27 | 0.27 | 0.50 | — | 0.43 |
| Dimethiconol[4] | — | — | — | — | — | 2.57 |
| Cocamidopropyl Betaine | 1.60 | 1.60 | 1.60 | 1.60 | 1.60 | 1.60 |
| Ethylene Glycol Distearate | 4.00 | 4.00 | 4.00 | 4.00 | 4.00 | 4.00 |
| Carbomer | 0.40 | 0.40 | 0.40 | 0.40 | 0.40 | 0.40 |
| Pearliser | 0.20 | 0.20 | 0.20 | 0.20 | 0.20 | 0.20 |
| Guar Hydroxypropyltrimonium Chloride | 0.20 | 0.20 | 0.20 | 0.20 | 0.20 | 0.20 |
| Tetrasodium EDTA | 0.10 | 0.10 | 0.10 | 0.10 | 0.10 | 0.10 |
| Preservative | 0.055 | 0.055 | 0.055 | 0.055 | 0.055 | 0.055 |
| Perfume | 0.80 | 0.80 | 0.80 | 0.80 | 0.80 | 0.80 |
| Citric Acid | 0.08 | 0.08 | 0.08 | 0.08 | 0.08 | 0.08 |
| Sodium Chloride | 0.90 | 0.90 | 0.90 | 0.90 | 0.90 | 0.90 |
| Sodium Hydroxide | 0.20 | 0.20 | 0.20 | 0.20 | 0.20 | 0.20 |

TABLE 1-continued

| Ingredient % wt | 1 | 2 | 3 | 4 | A | B |
|---|---|---|---|---|---|---|
| Aqua | Balance to 100% | Balance to 100% | Balance to 100% | Balance to 100% | Balance to 100% | Balance to 100% |

[1]DC 1788 ex. Dow corning
[2]DC 7128 ex. Dow corning. The concentration in this row refers to the amount of dimethicone itself by weight of the total composition. The weight ratio of dimethicone to poloxamer is 19:1 in this blend.
[3]DC 949 ex. Dow corning
[4]UL 9815 ex Wacker Example 2

This example demonstrates that shampoo 1 has better conditioning performance over both shampoo A and shampoo B.

Hair switches (10 g, 25 cm in length, and 3.5 cm in width for each switch) were used to test the conditioning performance of shampoos. The hair switches had been put into heptane and diethyl ether respectively for 30 to 60 minutes followed by removing excess solvent. Then, the hair switches had been cleaned twice by 14 wt. % SLES(1EO) in water with amount of 0.05 ml of per 1 g of hair switch followed by extensive rinsing. The hair switches were then put into hair sleeves, treated by test shampoo with amount of 0.05 ml of shampoo per 1 g of hair switch, and rinsed. The treating step by test shampoo was repeated once. After that, the hair switches were applied the same commercial available hair conditioner with amount 0.1 ml of hair conditioner per 1 g of hair switch followed by rinsing step. Subsequently, the hair switches were dried at 55° C. for 60 min and put the set of hair switch in Constant Temp/Humidity room for at least 30 minutes before evaluation starting. Six attributes on conditioning were accessed.

Total 6 persons were asked to evaluate 12 sets per person. The persons were given a pair of switches and asked them to choose the hair switches which they thought better for each attributes. The results for comparing shampoo 1 and A are shown in Table 2 and the results for comparing shampoo 1 and B are shown in Table 3. The tables only show the attributes which has a significant difference. Other attributes showed parity.

TABLE 2

| Hair conditioning characteristic | Hair treated by Shampoo 1 | Hair treated by Shampoo A | Significance level (%) |
|---|---|---|---|
| Wet smoothness | 52 | 20 | 99.9 |
| Wet combing | 61 | 11 | 99.9 |
| Dry combing | 49 | 23 | 99 |

TABLE 3

| Hair conditioning characteristic | Hair treated by Shampoo 1 | Hair treated by Shampoo B | Significance level (%) |
|---|---|---|---|
| Wet combing | 46 | 26 | 95 |
| Dry combing | 47 | 25 | 99 |
| Wet smoothness | 47 | 25 | 99 |

As can be seen from the Tables, shampoo 1 can deliver better "wet smoothness", "wet combing", and "dry combing" benefits to hair. The testers expressed a clear preference for shampoo 1 over both shampoo A and shampoo B. It was demonstrated that incorporating the silicone component of the present composition into shampoo would give better conditioning benefits than only incorporating two silicones thereof. The data clearly shows that composition of the present invention provides improved hair conditioning benefits.

Example 3

Shampoo compositions were made by standard processes and has the formulation given in Table 4.

TABLE 4

| Ingredient % wt | 5 | 6 |
|---|---|---|
| Sodium Laureth Sulphate | 11.55 | 11.55 |
| Cocamidopropyl Betaine | 1.51 | 1.51 |
| Beheneth-25 Methacrylate Copolymer | 0.2 | 0.2 |
| Citric Acid | 0.3 | 0.3 |
| Guar Hydroxypropyltrimonium Chloride | 0.2 | 0.2 |
| Glycerin | 0.5 | 0.5 |
| PEG-45M | 0.025 | 0.025 |
| Ethylene Glycol Distearate | 0.75 | 0.75 |
| Opacifier | 0.15 | 0.15 |
| Dimethiconol[1] | 0.273 | 0.409 |
| Blend of dimethicone with poloxamer[2] | 0.273 | 0.273 |
| Amodimethicone[3] | 0.205 | 0.068 |
| Preservative | 0.055 | 0.055 |
| Polyproylene Glycol | 0.36 | 0.36 |
| Perfume | 0.7 | 0.7 |
| Disodium EDTA | 0.2 | 0.2 |
| Sodium Hydroxide | 0.05 | 0.05 |
| Sodium Chloride | 0.6 | 0.6 |
| Aqua | Balance to 100% | Balance to 100% |

[1]DC 1788 ex. Dow corning
[2]DC 7128 ex. Dow corning. The concentration in this row refers to the amount of dimethicone itself by weight of the total composition. The weight ratio of dimethicone to poloxamer is 19:1 in this blend.
[3]DC 949 ex. Dow corning Example 4

This example demonstrates that shampoo 5 has better conditioning and cleaning performance over shampoo 6.

Shampoo composition 5 and 6 were assessed in a panel test. 36 panellists who had self-perceived damage hair with shoulder length or longer conducted the test. Each of them was given 60 ml plastic bottles of each of the two shampoos to use over a four week period. Each product was used at least twice (and a maximum of four times), and only one product was used in any one week. The panellists used the test product in place of their normal shampoo according to their normal habit and refrained from using conditioner or conventional mousse on the same day that they used the test product. The test was balanced so that equal numbers of panellists used each product each week. At the end of each week, each panellist completed a questionnaire scoring the shampoo tested that week against a series of attributes.

21 attributes including, for example amount of lather, time to rinsing, easy to web comb, volume, were compared among shampoo application, shampoo rinse, wet stage, and dry stage. It was found that shampoo 5 beat shampoo 6 on speed to lather (at 90% significance level), foam resistance (at 95% significance level), and slippery feel under running water (at 90% significance level). All other attributes showed parity. It was demonstrated that shampoo 5 has better conditioning and cleaning performance over shampoo 6 without compromising other attributes.

The invention claimed is:

1. A shampoo composition comprising a silicone component which comprises:
   (i) a dimethiconol,
   (ii) a blend of dimethicone with surface active block polymer, and
   (iii) an aminosilicone,
   wherein a weight ratio of the dimethicone to the aminosilicone is in the range of 1:100 to 20:1;
   wherein the weight ratio of the dimethicone to the surface active block copolymer in the blend is in the range from 2:1 to 200:1 and
   wherein the dimethicone has a viscosity of 30,000 to 100,000 centistokes at 25 degrees Celsius as measured by a capillary viscometer.

2. The composition according to claim 1 wherein the silicone component is present in the composition in amount from 0.1 to 5% by weight of the composition.

3. The composition according to claim 1 wherein the dimethiconol is present in the composition in amount from 0.04 to 2% by weight of the composition.

4. The composition according to claim 1 wherein the dimethicone is present in the composition in amount from 0.04 to 3% by weight of the composition.

5. The composition according to claim 1 wherein the aminosilicone is present in the composition in amount from 0.04 to 1% by weight of the composition.

6. The composition according to claim 1 wherein the weight ratio of the dimethiconol to the aminosilicone is in the range from 1:20 to 5:1.

7. The composition according to claim 1 wherein the weight ratio of the dimethicone to the aminosilicone is in the range from 1:10 to 3:1.

8. The composition according to claim 1 wherein the surface active block polymer is poloxamer.

9. The composition according to claim 1 wherein the composition comprises a cleansing surfactant.

10. The composition according to claim 1 wherein the composition comprises a cationic deposition polymer.

11. Method of treating the hair of an individual comprising the step of topically applying the composition of claim 1 to at least a portion of the hair.

12. The composition according to claim 1, wherein the weight ratio of the dimethicone to the surface active block copolymer in the blend is in the range from 5:1 to 50:1.

* * * * *